US005645559A

United States Patent [19]

Hachtman et al.

[11] Patent Number: 5,645,559
[45] Date of Patent: Jul. 8, 1997

[54] MULTIPLE LAYER STENT

[75] Inventors: Steven W. Hachtman, Chanhassen; Liann M. Johnson, Golden Valley; Scott T. Johnson, Anoka; Joseph E. Laptewicz, Jr., Eden Prairie; Paul J. Thompson, New Hope; Amjad Ahmad, Eagan, all of Minn.; John A. Scholl, Danville, Calif.; Richard J. Thompson, Watertown, Minn.

[73] Assignee: Schneider (USA) Inc, Plymouth, Minn.

[21] Appl. No.: 172,516

[22] Filed: Dec. 21, 1993

Related U.S. Application Data

[63] Continuation-in-part of Ser. No. 880,435, May 8, 1992, abandoned.

[51] Int. Cl.$^6$ ............................................. A61M 29/00
[52] U.S. Cl. .................................................. 606/198; 623/1
[58] Field of Search ................................ 606/198, 195, 606/191, 200; 623/1, 12

[56] References Cited

U.S. PATENT DOCUMENTS

| | | |
|---|---|---|
| 3,868,956 | 3/1975 | Alfidi et al. . |
| 4,140,126 | 2/1979 | Choudhury . |
| 4,553,545 | 11/1985 | Maass et al. . |
| 4,572,186 | 2/1986 | Gould et al. . |
| 4,580,568 | 4/1986 | Gianturco . |
| 4,649,922 | 3/1987 | Wiktor . |
| 4,655,771 | 4/1987 | Wallsten . |
| 4,665,918 | 5/1987 | Garza et al. . |
| 4,681,110 | 7/1987 | Wiktor . |
| 4,699,611 | 10/1987 | Bowden . |

(List continued on next page.)

FOREIGN PATENT DOCUMENTS

| | | |
|---|---|---|
| 5871290 | 11/1991 | Australia . |
| 3218593 | 8/1993 | Australia . |
| 0183372 | 6/1986 | European Pat. Off. . |
| 0408245A1 | 1/1991 | European Pat. Off. . |
| 3918736A1 | 12/1990 | Germany . |
| 1205743 | 9/1970 | United Kingdom . |
| 1565828 | 4/1980 | United Kingdom . |
| 87/04935 | 8/1987 | WIPO . |
| 9317636 | 9/1993 | WIPO . |

OTHER PUBLICATIONS

Binmoeller, K. F., et al., "Silicone–Covered Expandable Metallic Stents in the Esophagus: An Experimental Study", pp. 416–420, 1992, *Edoscopy*.

Fleischer, David E., et al., "A New Coated Self–Expanding Metal Stent for Malignant Esophageal Strictures", pp. 494–496, 1992, *Gastrointestinal Endoscopy*.

Pilkington, Theo C., Duke–North Carolina NSF/ERC for Emerging Cardiovascular Technologies Annual Report, Jul. 29, 1988.

Domschke, W., et al., "Self–Expanding Mesh Stent for Esophageal Cancer Stenosis", pp. 134–136, 1990, *Endoscopy*.

Song, Ho–Young et al., "Esophagogastric Neoplasms: Palliation with a Modified Gianturco Stent", pp. 349–354, 1991, *Radiology*.

*Primary Examiner*—Michael Buiz
*Assistant Examiner*—Nancy Connolly Mulcare
*Attorney, Agent, or Firm*—Lawrence C. Akers; Peter C. Richardson; Philip C. Strassburger

[57] ABSTRACT

A radially self-expanding stent having multiple layers includes a medial region and proximal and distal cuffs having diameters greater than the medial region diameter when the stent is in the relaxed state. A silicone coating circumscribes at least the medial region of the stent. A deployment device for the stent includes an inner tube surrounded by the stent along with an outer tube that radially compresses the stent. A low durometer sleeve, fixed to the inner tube and in surface engagement with the compressed stent, tends to fix the axial position of the stent relative to the inner tube whenever the outer tube is moved axially relative to the inner tube. Consequently, precision in stent placement and the ability to recapture a partially deployed stent are enhanced.

22 Claims, 15 Drawing Sheets

U.S. PATENT DOCUMENTS

| | | | |
|---|---|---|---|
| 4,723,549 | 2/1988 | Wholey et al. | |
| 4,728,328 | 3/1988 | Hughes et al. | |
| 4,732,152 | 3/1988 | Wallsten et al. | |
| 4,733,665 | 3/1988 | Palmaz . | |
| 4,747,849 | 5/1988 | Galtier . | |
| 4,768,507 | 9/1988 | Fischell et al. | |
| 4,793,348 | 12/1988 | Palmaz . | |
| 4,794,928 | 1/1989 | Kletschka . | |
| 4,800,882 | 1/1989 | Gianturco . | |
| 4,825,861 | 5/1989 | Koss . | |
| 4,830,003 | 5/1989 | Wolff et al. | |
| 4,848,343 | 7/1989 | Wallsten et al. | |
| 4,850,999 | 7/1989 | Planck . | |
| 4,856,516 | 8/1989 | Hillstead . | |
| 4,875,480 | 10/1989 | Imbert . | |
| 4,877,030 | 10/1989 | Beck et al. | 606/195 |
| 4,878,906 | 11/1989 | Lindemann et al. | |
| 4,886,062 | 12/1989 | Wiktor . | |
| 4,921,484 | 5/1990 | Hillstead . | |
| 4,954,126 | 9/1990 | Wallsten . | |
| 4,955,899 | 9/1990 | Della Corna et al. | 623/1 |
| 4,957,508 | 9/1990 | Kaneko et al. | |
| 4,973,301 | 11/1990 | Nissenkorn . | |
| 5,015,253 | 5/1991 | MacGregor | 623/1 |
| 5,026,377 | 6/1991 | Burton et al. | |
| 5,061,275 | 10/1991 | Wallsten et al. | |
| 5,064,435 | 11/1991 | Porter | 623/12 |
| 5,071,407 | 12/1991 | Termin et al. | |
| 5,089,006 | 2/1992 | Stiles . | |
| 5,108,416 | 4/1992 | Ryan et al. | |
| 5,112,900 | 5/1992 | Buddenhagen et al. | |
| 5,123,917 | 6/1992 | Lee . | |
| 5,158,548 | 10/1992 | Lau et al. | |
| 5,171,262 | 12/1992 | MacGregor . | |
| 5,201,757 | 4/1993 | Heyn et al. | |
| 5,211,658 | 5/1993 | Clouse . | |
| 5,282,823 | 2/1994 | Schwartz et al. | 606/198 |
| 5,316,026 | 5/1994 | Palmaz et al. | 606/198 X |
| 5,330,500 | 7/1994 | Song | 606/198 |
| 5,360,443 | 11/1994 | Barone et al. | 606/195 X |
| 5,405,377 | 4/1995 | Cragg | 606/191 X |

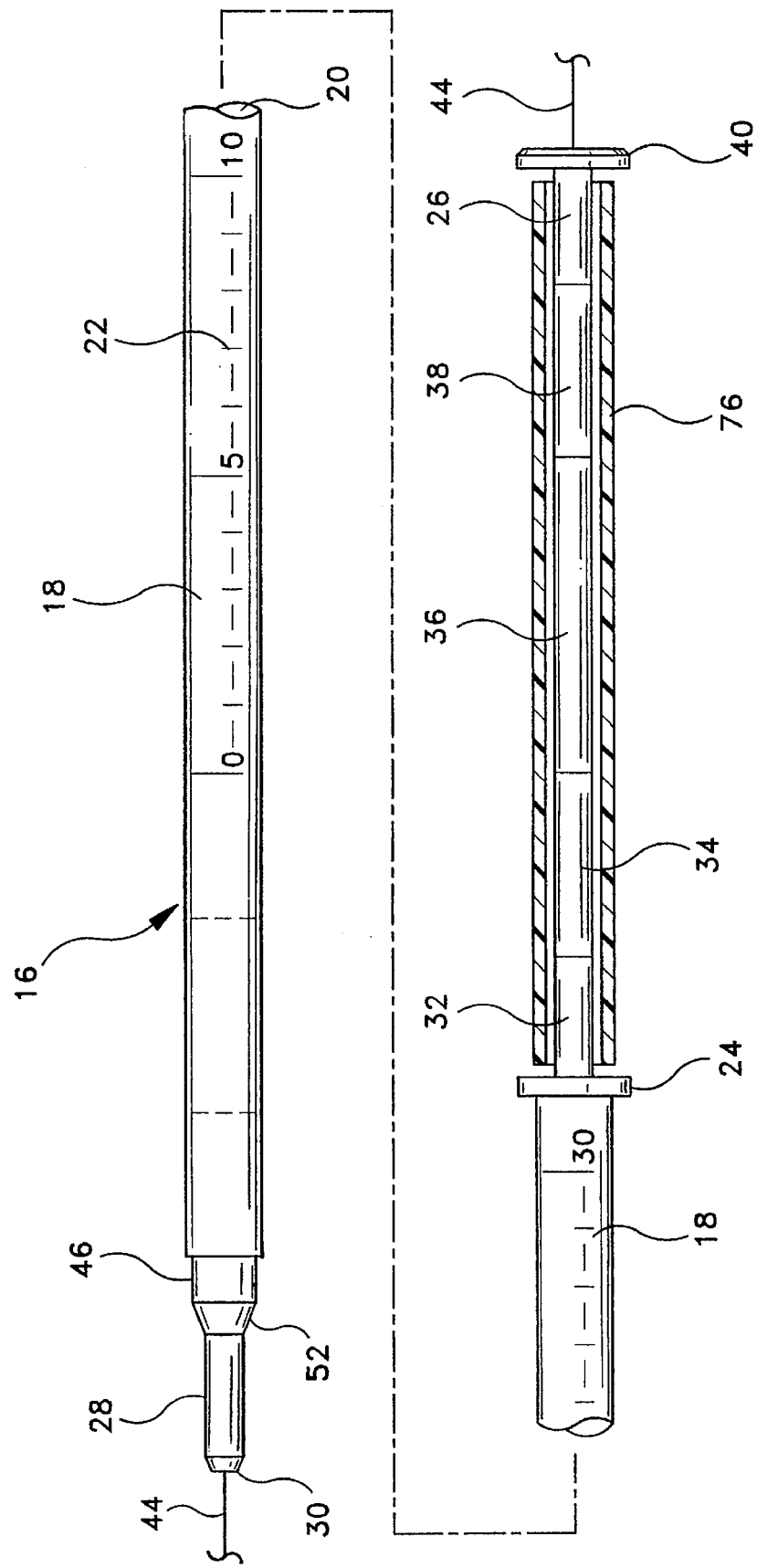

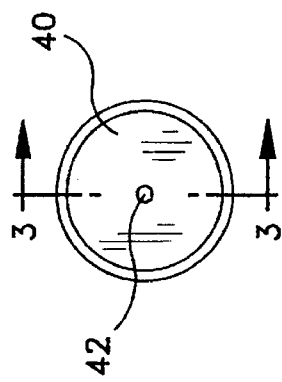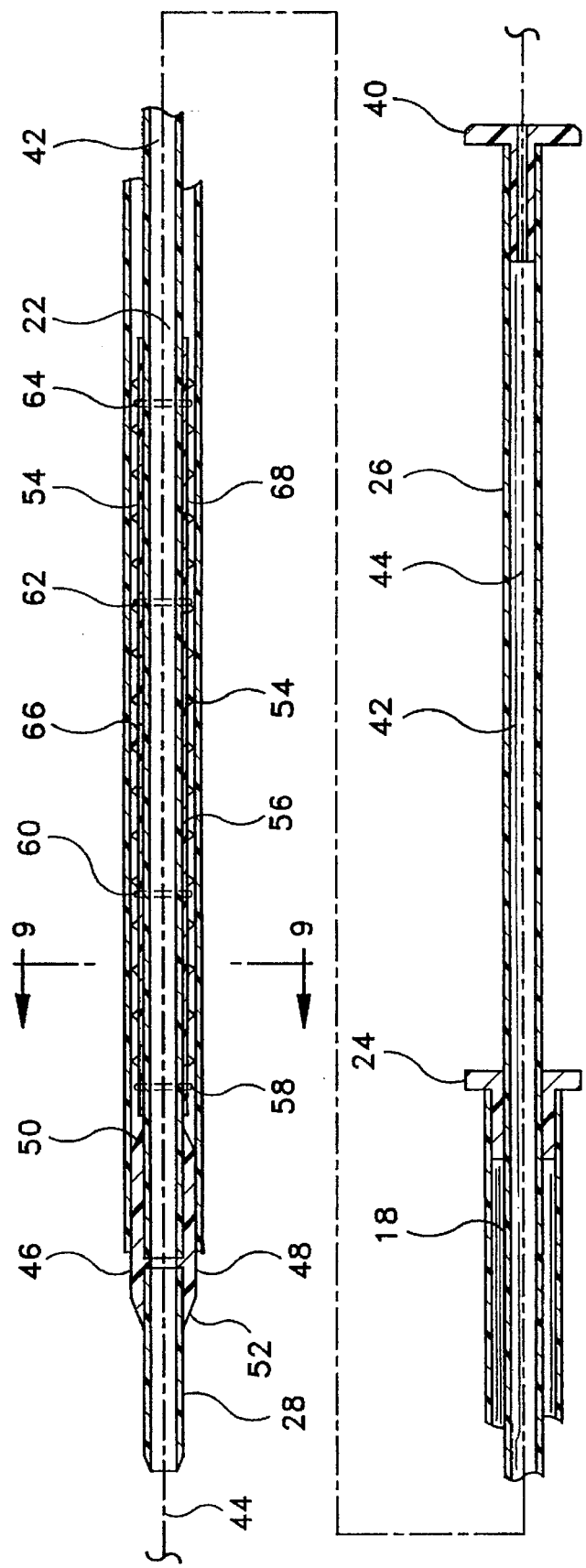

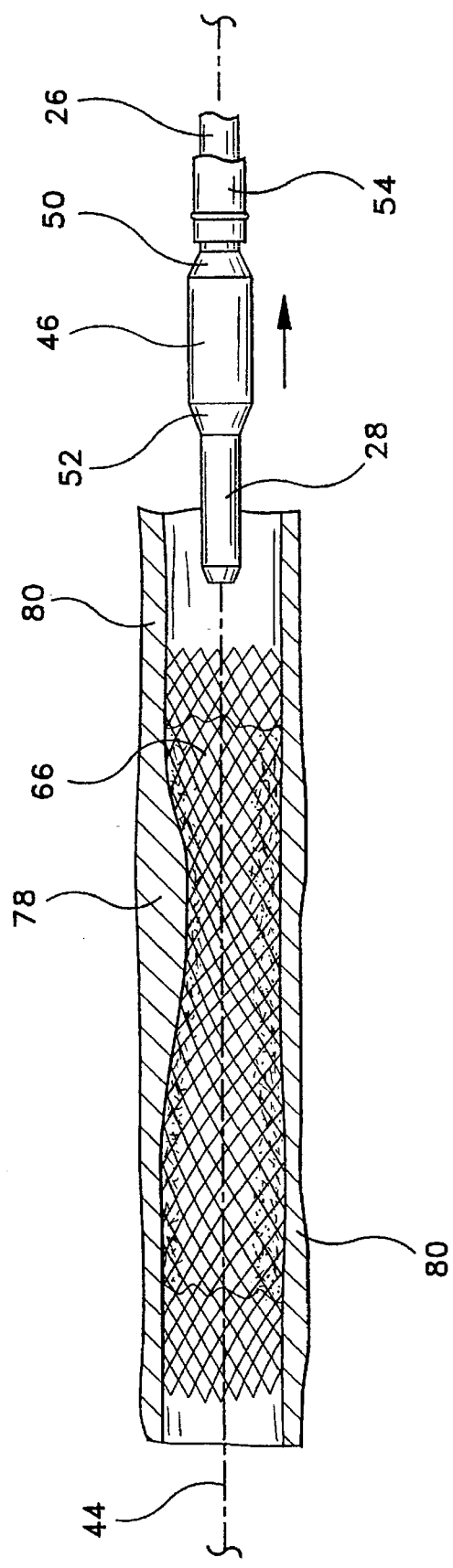

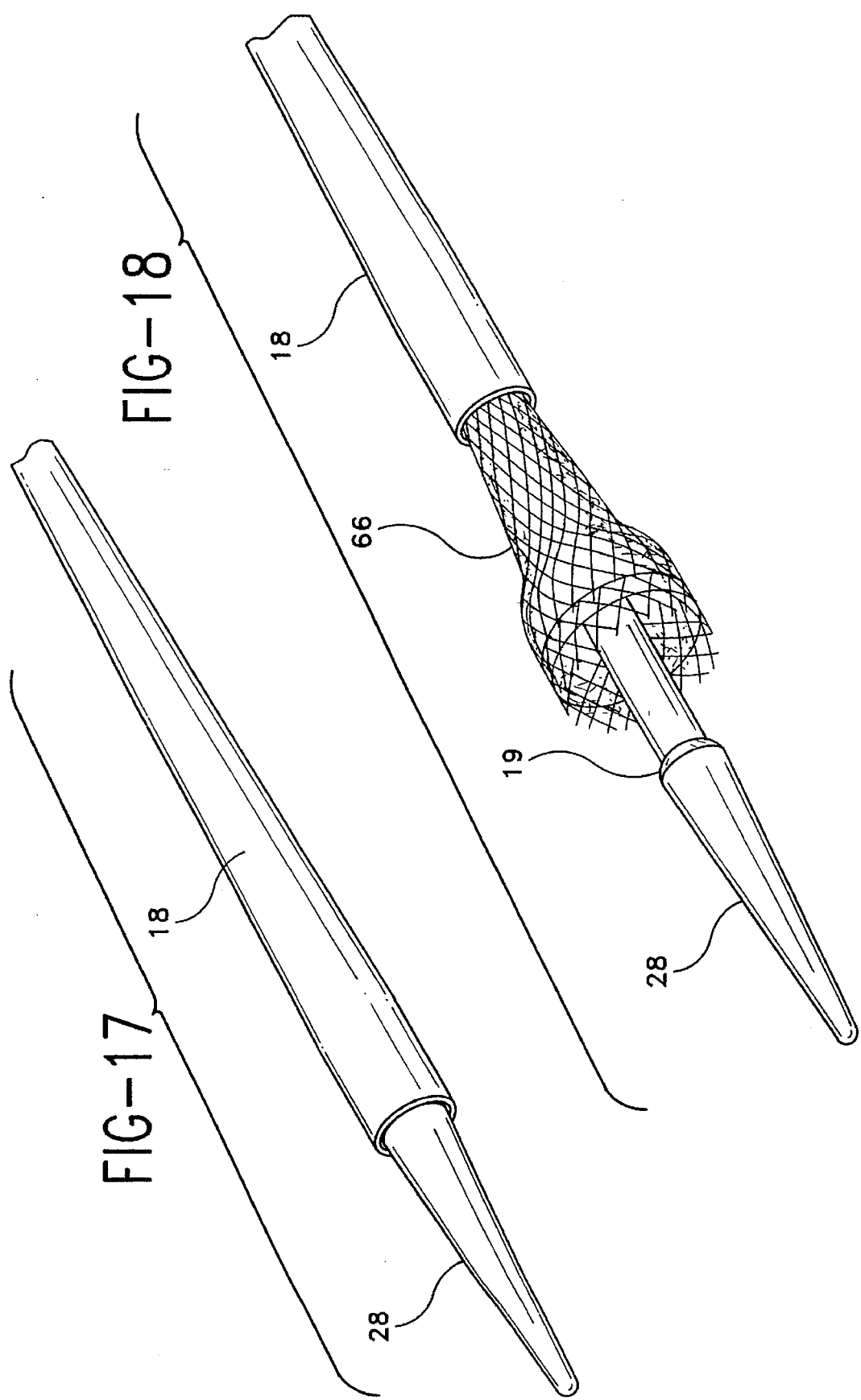

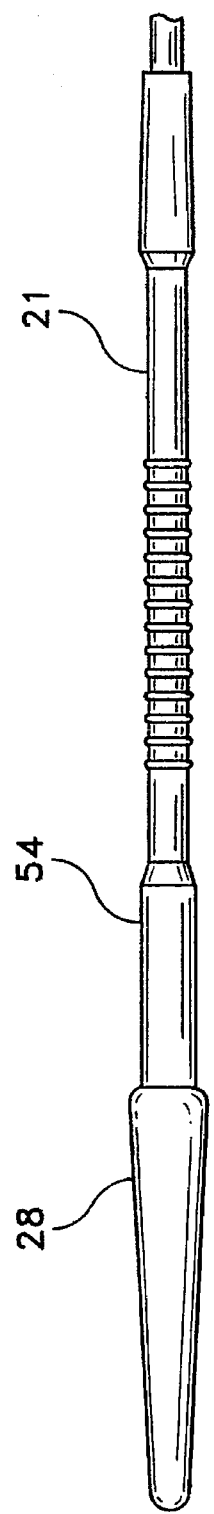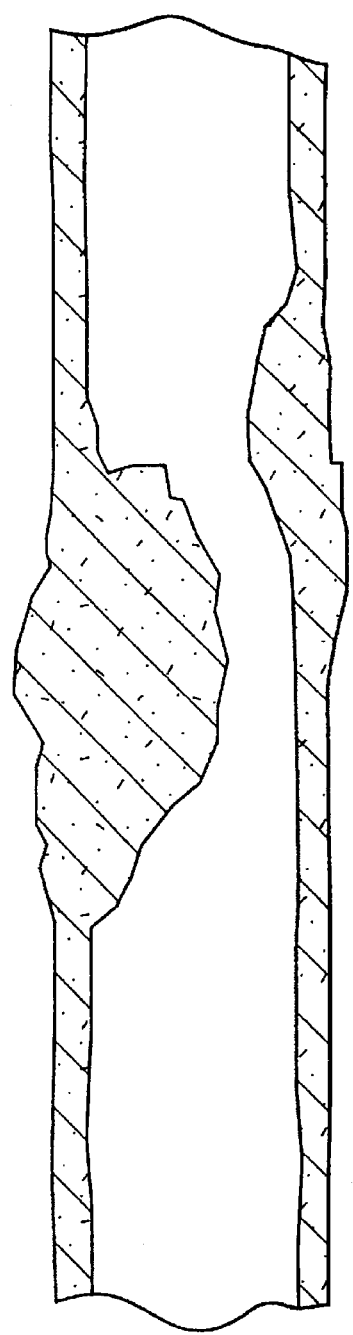
FIG-22
FIG-23

MULTIPLE LAYER STENT

This application is a continuation in part of U.S. patent application Ser. No. 07/880,435 filed on May 8, 1992, now abandoned.

BACKGROUND OF THE INVENTION

The present invention relates to a body implantable treatment device intended for fixation in body lumens such as the esophagus, bile duct and blood vessels.

There are many situations requiring interventional procedures to repair damage to a body vessel. For example, carcinomas in the esophagus and the bile duct can lead to progressive closing of the lumen. A fistula in the trachea and esophagus can render those vessels inoperable. Similarly, an aneurysm in a blood vessel may rupture and render the blood vessel useless for maintaining blood flow therethrough. One means of repairing such a body vessel is by implanting a stent in the area of the damage. A radially self-expanding stent such as described in U.S. Pat. Nos. 4,655,771 and 5,061,275 is preferred because its radially self-expanding characteristics facilitate delivery of the stent to the treatment site. Such a stent can be constrained at a diameter smaller than its diameter in an unconstrained state and placed on a suitable delivery device. The delivery device in turn can be placed in the body percutaneously so the constrained stent is located adjacent the treatment site. When the means constraining the stent on the delivery device is removed, the stent radially self-expands into place.

However, such a self-expanding stent has certain limitations. These stents generally have a braided mesh configuration formed by a plurality of helically wound thread elements. This configuration results in a plurality of interstices constituting open spaces between the thread elements. Thus these stents are subject to tissue ingrowth through these interstices. Moreover, these stents may be inadequate if they are to be used to support the flow of fluid or some other media therethrough past a tracheal/esophageal fistula or past an aneurysm in a blood vessel.

A further difficulty with such a self-expanding stent concerns their accurate placement and deployment. Typically an outer tube surrounds the self-expanding stent and radially compresses the stent into a reduced-radius delivery configuration. With the stent positioned at a treatment site, the outer tube is axially withdrawn, permitting the stent to radially self-expand. However, there is friction at the stent/outer tube interface. This friction, at a minimum, makes withdrawal of the tube difficult and, if the friction is too high, could cause the stent to travel with the tube as it is axially withdrawn. As a result, it is difficult precisely to maintain the position of the stent during deployment.

In addition, once the stent is partially deployed, i.e. where the distal portion of the stent is not compressed by the outer tube, friction between the stent and outer tube may prevent the outer tube from being axially moved over the distal portion of the stent to radially compress the stent. Instead, the outer tube may simply push the stent in the distal direction if the outer tube is moved axially distally to reposition the stent by moving the tube back over the stent after partial deployment.

Therefore, it is an object of the present invention to provide a radially self-expanding stent having a barrier region to inhibit tissue ingrowth and to support the flow of fluid or some other media therethrough.

It is a further object of this invention to provide a stent deployment device capable of accurately positioning a radially self-expanding stent near a treatment site and recapturing the stent for repositioning, even if the stent has been partially deployed and is radially expanded over the majority of its axial length.

SUMMARY OF THE INVENTION

These and other objects are achieved by the multiple layer stent and stent delivery device of the present invention.

The stent comprises two layers of mesh formed of braided helically wound thread elements. Each mesh has a proximal cuff and a distal cuff with a medial region positioned between the cuffs. This medial region preferably has a diameter less than the diameter of the proximal cuff and distal cuff. At least one silicone layer is located between the two mesh layers to provide a barrier that prevents the growth of tissue through the stent and to support the flow of fluid or some other media through the stent lumen. The proximal and distal cuffs tend to prevent migration of the stent from the treatment site.

The stent delivery device comprises an elongate and flexible inner tube, with a central lumen for accommodating a guidewire if desired, and an outer tube coaxially disposed around at least a distal portion of the inner tube that serves as the stent confining means. The outer tube surrounds the stent to confine and compress the stent into a delivery configuration in which the stent has a reduced radius along its axial length.

The inner tube has a recessed area along a distal region thereof for receiving the stent. In addition, a low durometer sleeve surrounding the inner tube along at least the distal region is provided with a plurality of circumferential ribs located over the recessed area. As a result of these features, the stent does not travel axially with the outer tube as it is moved proximally or distally over the stent. Rather, the stent remains substantially fixed in the axial direction with respect to the inner tube. This structure affords several advantages. First, the inner tube can be used as a means to maintain the radially self-expanding stent in the desired axial position during deployment. The inner tube can itself be employed as a reliable indicator of stent position, both prior to and during deployment. Further, should the need arise to move the stent after a partial deployment, the outer tube can be moved back into the confinement position over the partially deployed stent, without tending to carry the stent along with it.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout and in which:

FIG. 1 is a side elevational view of a stent delivery device constructed in accordance with a first embodiment of the present invention;

FIG. 2 is an end elevation of the stent delivery device of the first embodiment;

FIG. 3 is a sectional view taken along the line 3—3 in FIG. 2;

FIGS. 5–8 are partial sectional views showing the stent delivery device of the first embodiment during several stages of deploying a radially self-expanding stent constructed in accordance with a first embodiment of the present invention;

FIG. 17 is a perspective view of the distal portion of a third embodiment of the stent delivery device of this invention;

FIG. 18 is a perspective view similar to the view shown in FIG. 17 with a third embodiment of the stent of this invention partially deployed from the third embodiment of the stent delivery device of this invention;

FIG. 22 is a side elevational view of the distal portion of the inner tube of the third embodiment of the stent delivery device of this invention;

FIG. 23 shows a body lumen to be treated;

DETAILED DESCRIPTION OF THE INVENTION

Figure 4:
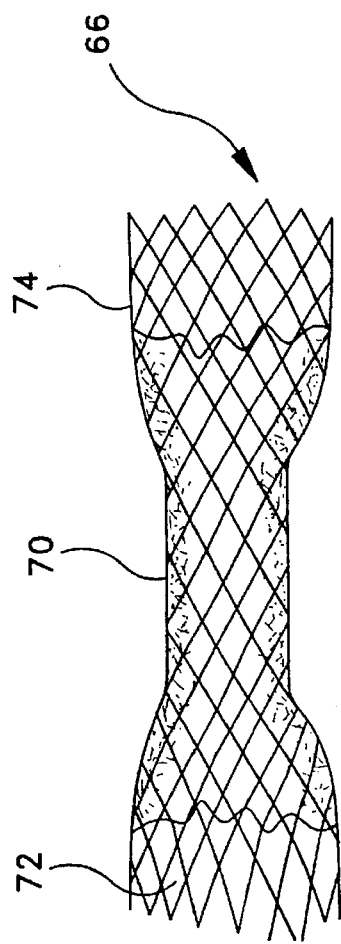
FIG. 4 is a side elevational view of the stent constructed in accordance with a first embodiment of the present invention in a relaxed configuration.

Turning now to the drawings, there is shown in FIG. 1 a delivery device 16 for delivering a stent or other generally tubular prostheses to an intended treatment location within a body lumen, and then controllably releasing the stent for radial self-expansion and fixation within the body lumen.

The device includes an elongate outer catheter or tube 18 constructed of a biocompatible polymer, e.g. butyl rubber, polypropylene, FEP or Teflon, with an outside diameter of about 12 mm or less along its distal portion with a smaller outside diameter along its proximal portion. This tapered configuration contributes to the flexibility of delivery device 16. The distal end of outer tube 18 is preferably radiused to minimize the presentation of a sharp corner to the body vessel in which delivery device 16 is maneuvered. A central lumen 20 runs the length of outer tube 18. On the outside of outer tube 18 are visible markings 22 designating length in centimeters. When using delivery device 16, a physician can determine the extent of insertion into the body based upon these markings. Throughout deployment, the proximal end of outer tube 18 remains outside the patient. A hub or handle 24 at the proximal end of outer tube 18, facilitates manipulation of outer tube 18 by hand. Outer tube 18 has an inner diameter along its distal portion sized to accommodate a stent therein. In addition, the inside surface of outer tube 18 can be coated with silicone or some other lubricous substance to facilitate movement of outer tube 18 past a stent confined therein.

An inner catheter or tube 26 runs through lumen 20, contained within outer tube 18. Inner tube 26 has an outside diameter of approximately 6 mm or less, and is constructed of a biocompatible polymer, e.g. polypropylene, FEP, Hytrel or nylon.

At the distal end of inner tube 26 is a distal tip 28. The distal tip is flexible, yet sufficiently rigid to be self-supporting rather than pliable when encountering tissue. As a result, distal tip 28 can be used to dilate the body lumen along regions where a tumor or other relatively soft stricture is present. Over the majority of its length, distal tip 28 has a diameter substantially equal to the diameter of inner tube 26, with a distal converging end 30 formed as part of the tip. Alternatively, as shown in FIG. 22, distal tip 28 may have an annular shoulder 19 at its proximal end and then have a gradually converging cross-section in the distal direction. Distal tip 28 is preferably formed from silicone having a hardness of 70D.

A recessed area 21 may also be located along a distal portion of inner tube 26 just proximal of distal tip 28. See FIG. 22. Recessed area 21 should have a length comparable to the length of the covered portion of the stent of this invention, which is to be implanted in the body lumen, when the stent is in its constrained, reduced diameter configuration.

A proximal region 32 of inner tube 26 extends proximally beyond hub 24. Visible markings on the outer surface of inner tube 26 define three adjacent segments of the proximal region, as indicated at 34, 36 and 38 in FIG. 1, respectively. These segments can be different colors if desired, to enhance their recognition. These segments, and more particularly the position of hub 24 along them, indicate the axial position of outer tube 18 relative to inner tube 26. The segments further indicate the stages of stent deployment, as is later explained.

At the proximal end of inner tube 26 is a hub or handle 40, which facilitates manipulation of inner tube 26 by hand. A lumen 42 (FIG. 3) runs the length of inner tube 26, to accommodate a guidewire 44. Although not shown in FIGS. 17, 18, 22, 24–27, it is to be understood that a longitudinally extending guidewire lumen may be included therethrough if desired.

Figure 9:
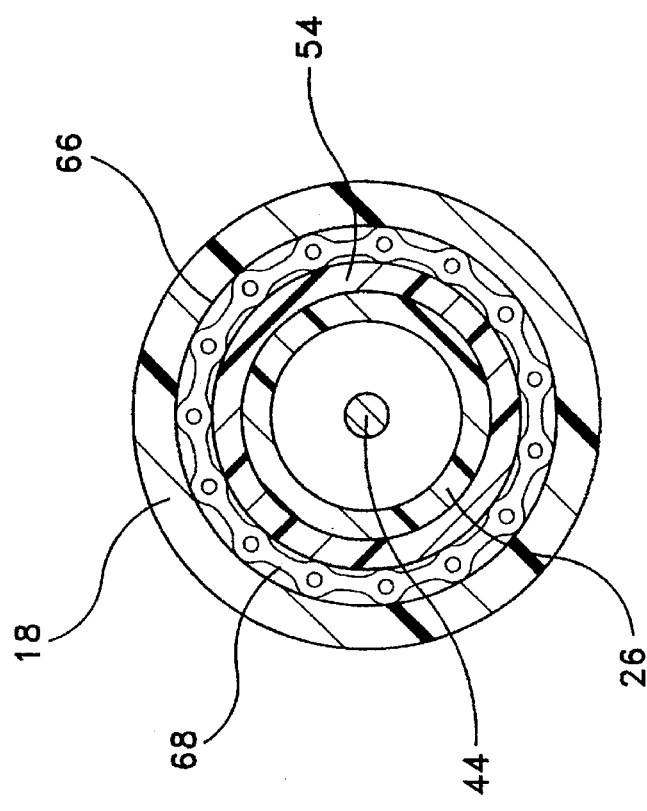
FIG. 9 is a sectional view taken along the line 9—9 in FIG. 3, showing a stent retaining layer.

Referring back to FIGS. 3 and 9, an annular restraining sleeve 54 surrounds a distal region 56 of inner tube 26. The sleeve is formed from a low durometer, preferably 30D, material. The preferred material for restraining sleeve 54 is silicone although other soft polymer materials could be used or even a medical adhesive material. Annular restraining sleeve 54 should be at least as long as the stent, which is to be implanted into the body vessel, when the stent is constrained on inner tube 26. In the embodiment of this invention shown in FIG. 22, distal tip 28 is formed integrally with restraining sleeve 54. In addition, in that embodiment, restraining sleeve 54 comprises a plurality of circumferential ribs formed thereon. These ribs should be positioned on restraining sleeve 54 so that they are aligned with recessed area 21 of inner tube 26. These ribs help to hold the stent in place during deployment and repositioning of the stent. These ribs should be arranged so that they are adjacent to the medial portion of the stent when the stent is placed on inner tube 26.

Alternatively, as shown in FIG. 3, sleeve 54 can be formed by wrapping double sided adhesive tape around inner tube 26 so that sleeve 54 adheres to inner tube 26 and also exhibits tackiness over its exterior surface. Radiopaque markers 58, 60, 62 and 64 surround sleeve 54. These markers can be surrounded by sleeve 54 if desired. In addition, markers 60 and 62 could be used alone if desired.

Surrounding sleeve 54 is a radially self-expanding stent 66. Stent 66 preferably is of open weave or mesh construction, formed of multiple helically wound strands or filaments of a flexible material such as body compatible stainless steel. Other materials such as nitinol and various polymers could also be used.

The durometer of sleeve 54 is substantially less than the durometer of outer tube 18 and inner tube 26. Sleeve 54 is sized such that whenever outer tube 18 radially compresses stent 66, outer tube 18 also is pressing stent 66 into a surface engagement with sleeve 54, to the point of at least slightly elastically deforming sleeve 54. As a result, friction between stent 66 and sleeve 54 substantially exceeds friction between stent 66 and the interior surface of outer tube 18. Given the length and positioning of sleeve 54, stent 66 when compressed contacts sleeve 54 over a substantial portion of its axial length. Thus, there is no tendency in stent 66 to travel with outer tube 18 as it moves axially relative to inner tube 26. Rather, stent 66 remains essentially fixed in the axial direction relative to inner tube 26. As a result, the axial position of inner tube 26 serves as a reliable indication of the location of stent 66, not only before deployment, but throughout most of the deployment procedure.

Hub 24 is fixed to outer tube 18, and has an opening to accommodate inner tube 26 such that inner tube is slidable axially relative to hub 24. Hub 40 has an opening formed therethrough, to accommodate guidewire 44.

In use, deployment device 16, including stent 66 radially compressed as shown in FIG. 3, is inserted into a body lumen, either with or without guidewire 44, and is directed toward the desired treatment location as it is moved distally.

Figure 5:
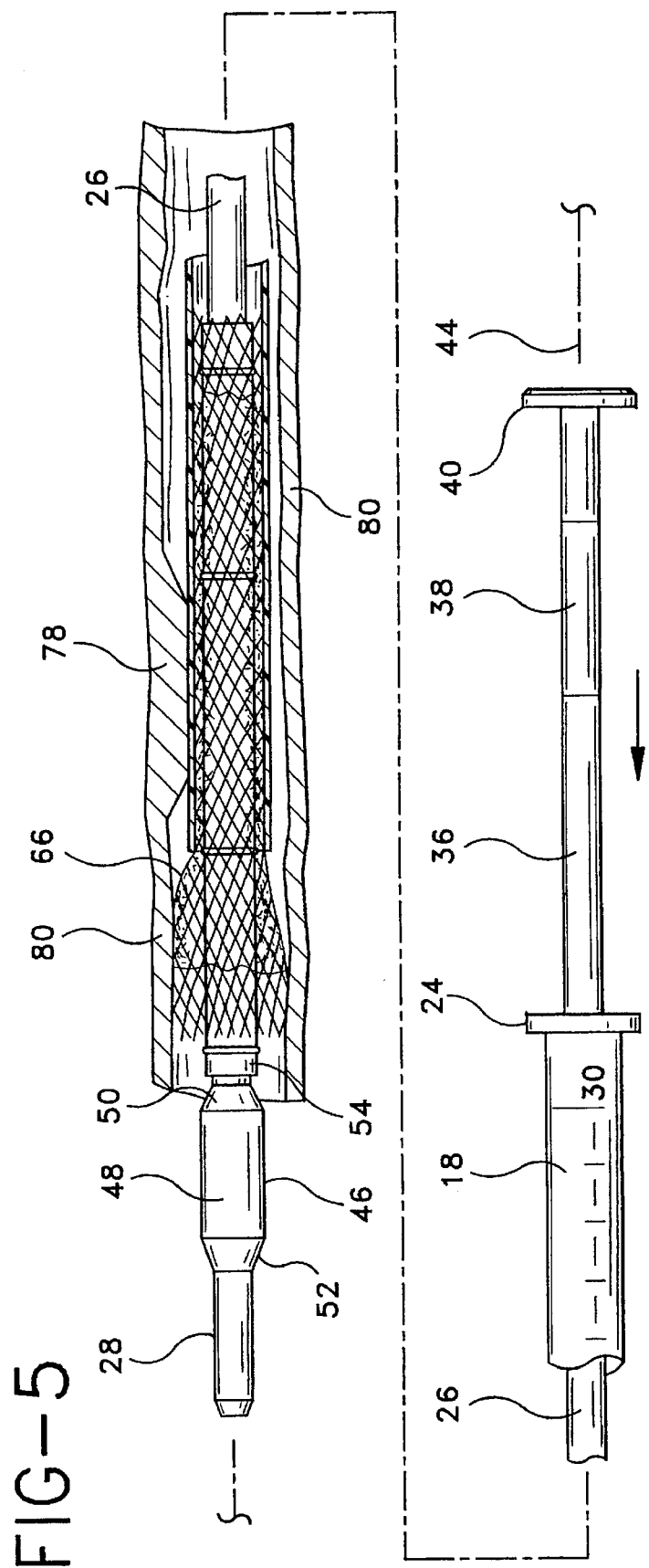

With the distal end of outer tube 18 past the stricture, stent deployment is initiated. Inner tube 26 is held substantially fixed and hub 24 is manipulated by hand to withdraw outer tube 18 in the proximal direction. When hub 24 encounters segments 34 along the proximal region 32 of inner tube 26, the distal end of outer tube 18 is near the distal end of stent 66, meaning that deployment is about to begin. Before further withdrawal of outer tube 18, the stent position can be reexamined to insure that medial region 70 of stent 66 is aligned with the stricture. With stent 66 properly aligned, outer tube 18 is withdrawn proximally until hub 24 encounters segment 36. As shown in FIG. 5, by the time hub 24 encounters segment 36, distal end region 72 (the distal cuff) of stent 66 is released from outer tube 18 and radially self-expands until it encounters tissue 80.

Figure 6:
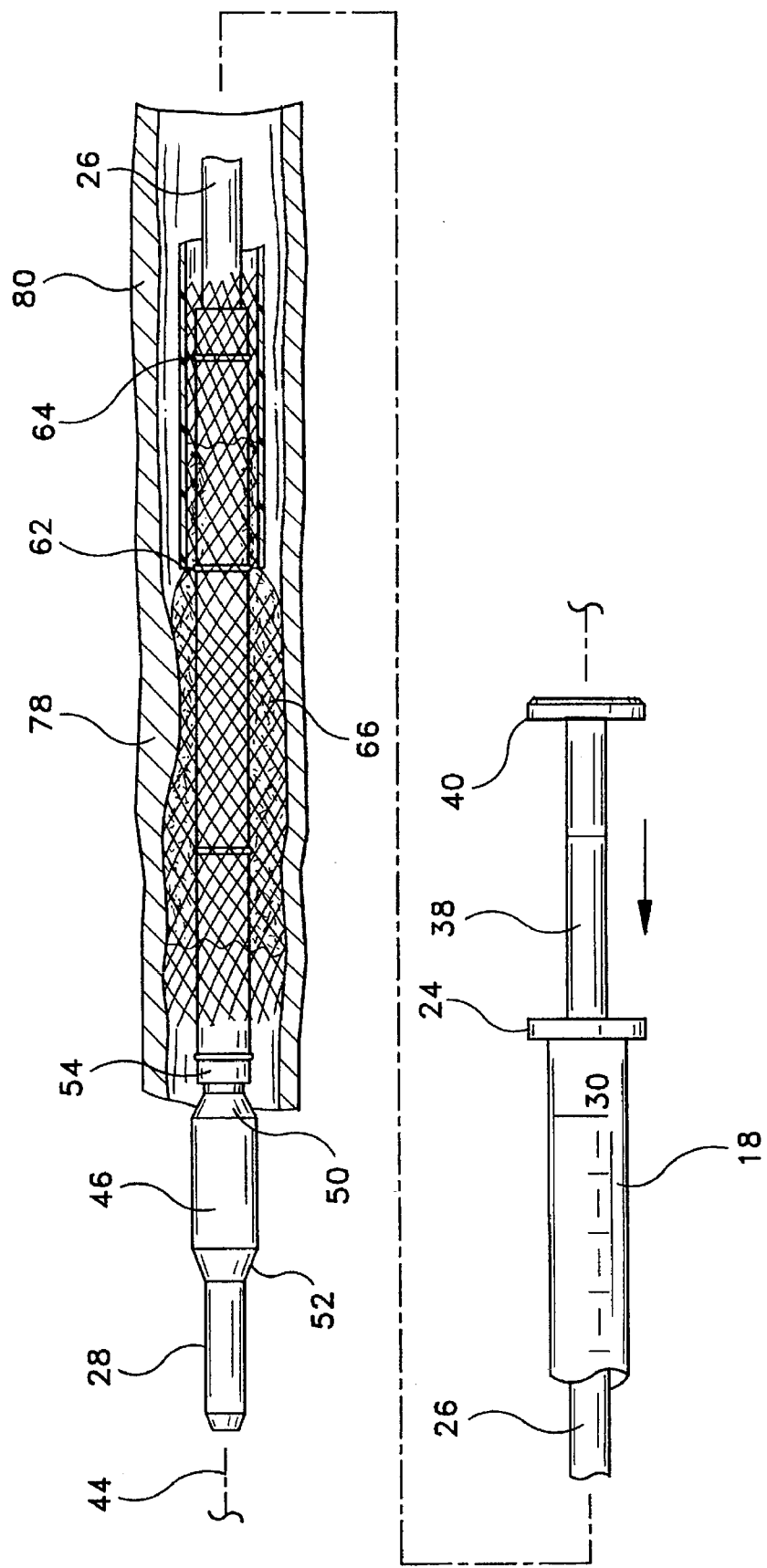
Figure 24:
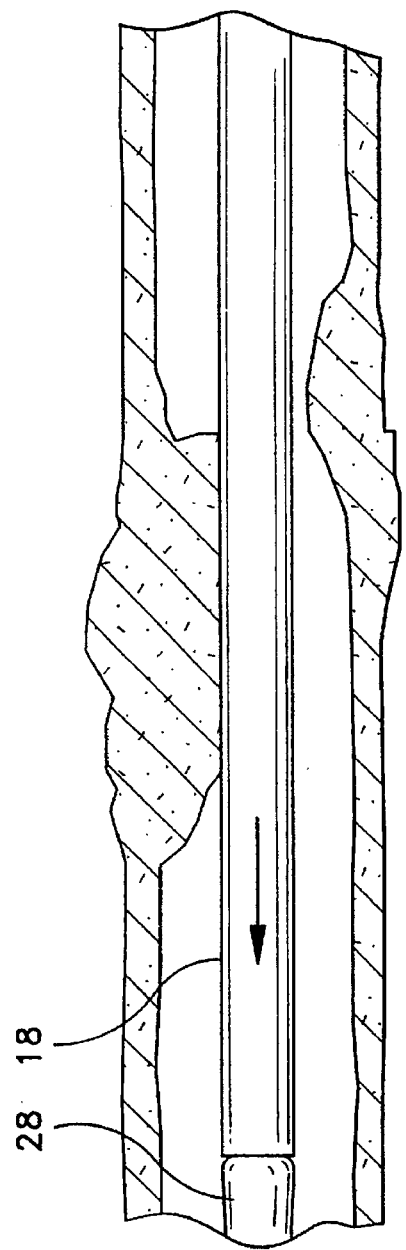
FIGS. 24–27 show the positioning and repositioning of the third embodiment of the stent delivery device in the body lumen of FIG. 23.
Figure 25:
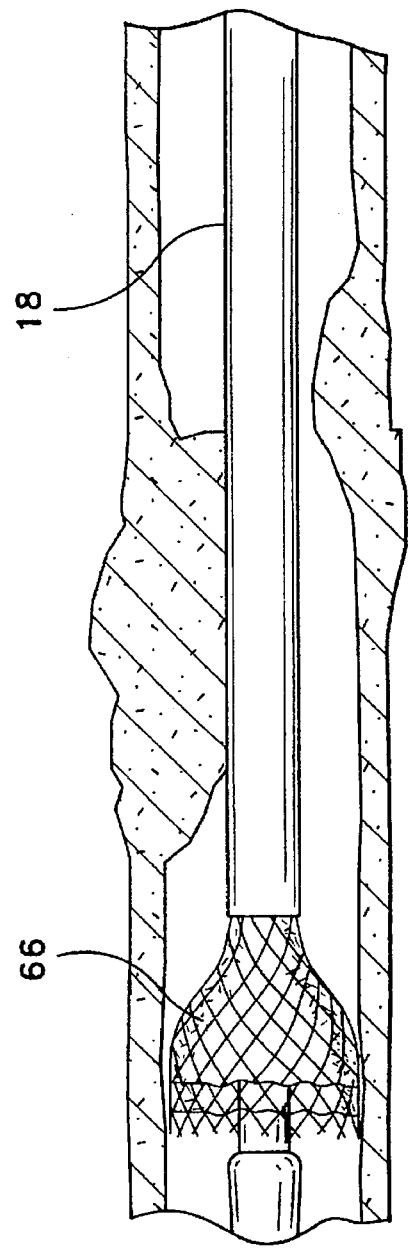
Figure 26:
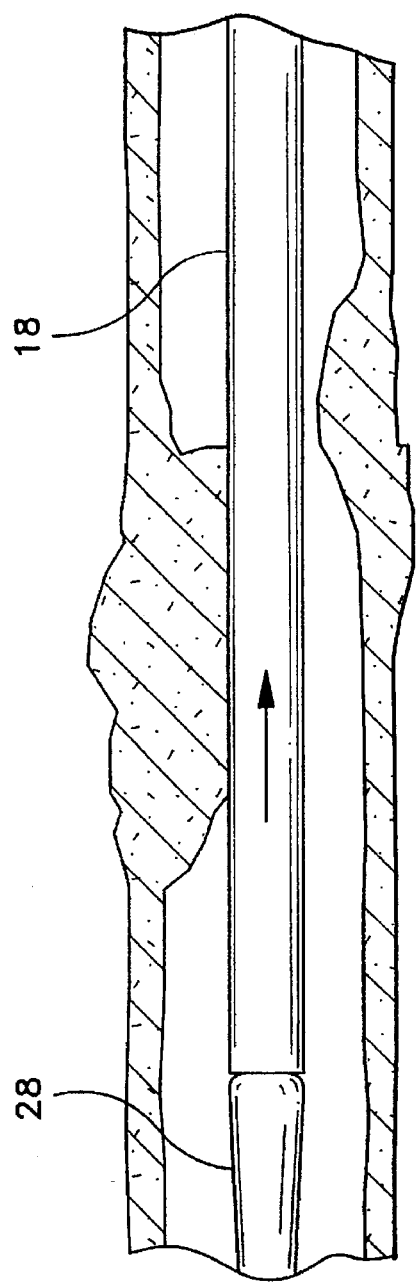
Figure 27:
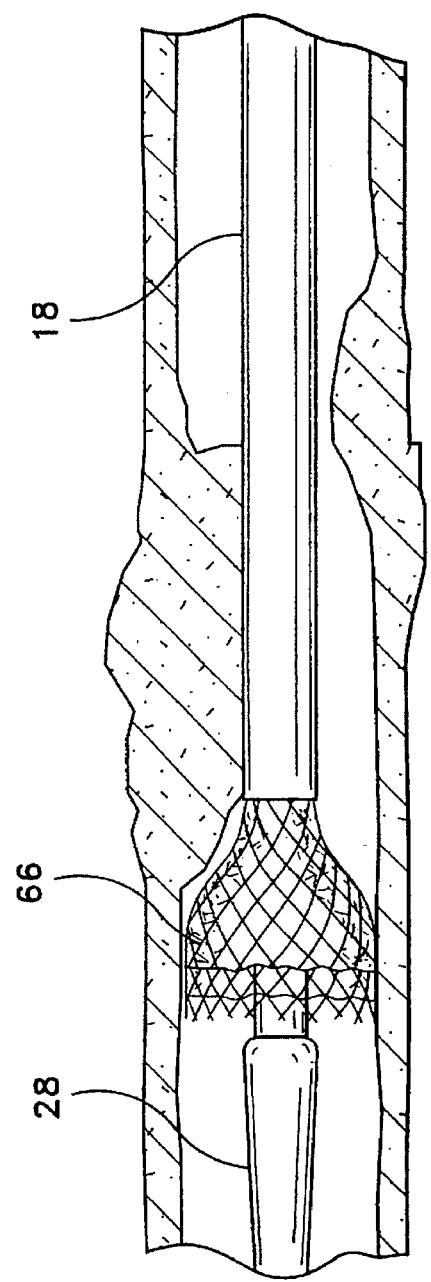
Figure 28:
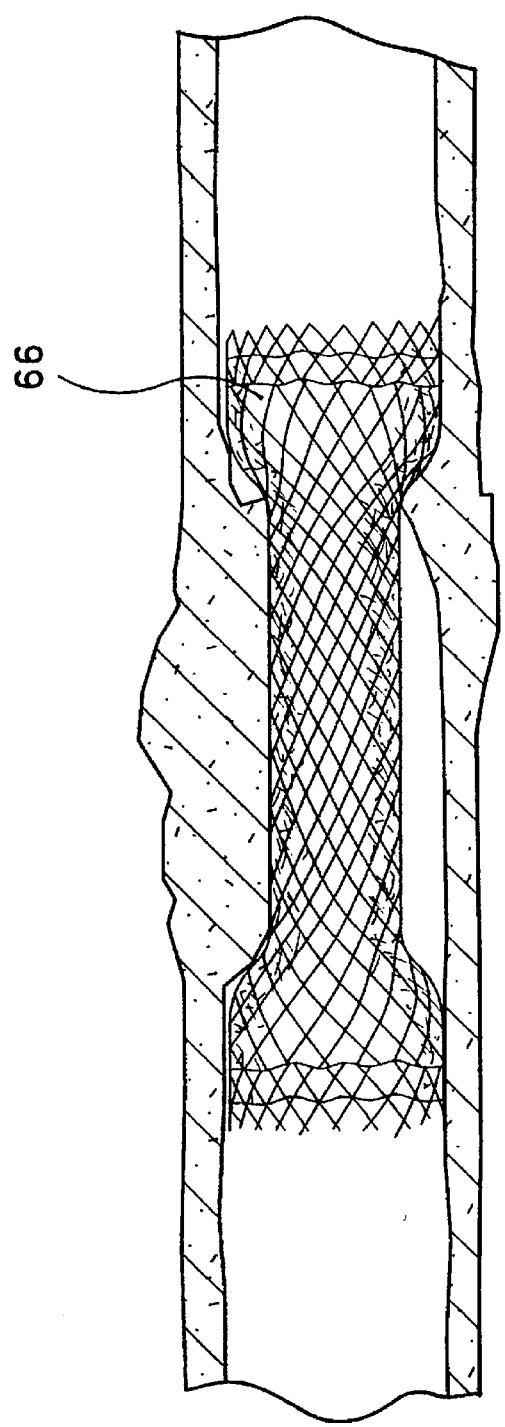
FIG. 28 shows the third embodiment of the stent of this invention deployed in the body lumen of FIG. 23.

FIG. 6 illustrates further withdrawal of outer tube 18, to the point where hub 24 encounters marked segment 38. This corresponds to release of stent 66 over its distal region and medial region, i.e. roughly three-quarters deployment. One of the advantages of sleeve 54 is that even at this advanced stage, it remains possible to recover or retract stent 66 by moving outer tube 18 distally relative to inner tube 26. Such stent recapture occasionally is necessary, in order to reposition stent 66 in the body lumen. This procedure is shown in FIGS. 24–27 where FIGS. 24 and 25 show partial deployment of stent 66 and FIGS. 26 and 27 show the repositioning of stent 66. More generally, stent 66 is virtually always recapturable by outer tube 18, even when a majority of its axial length is released. With the stent retaining means of the present invention, stents have been found to be recapturable after up to 80 percent deployment.

Figure 7:
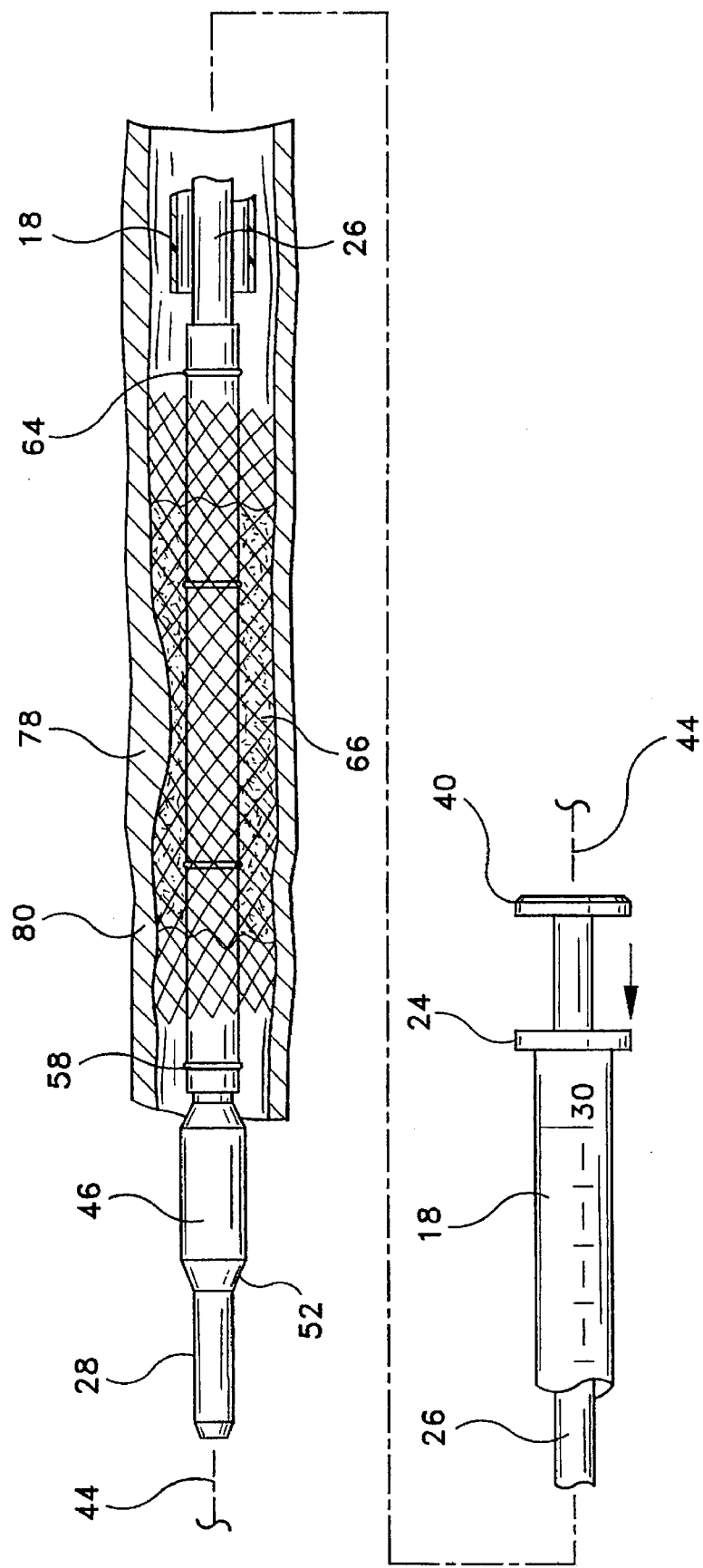
Figure 10:
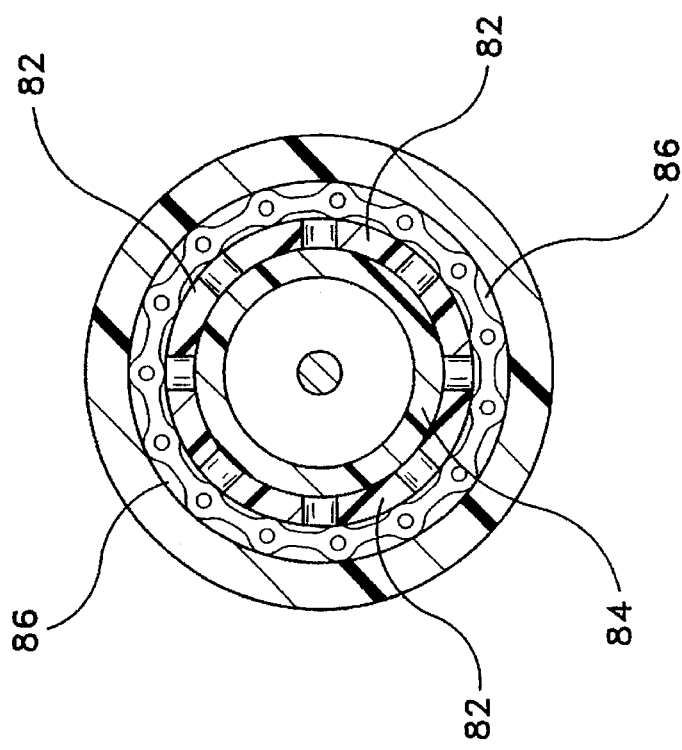
FIG. 10 is a sectional view similar to FIG. 9, but showing a second embodiment for the stent delivery device utilizing stent retaining strips in lieu of the retaining layer shown in FIG. 9.

FIG. 7 illustrates full withdrawal of outer tube 18 to completely release stent 66, corresponding to proximal movement to the point where hub 24 is at the proximal end of proximal segment 38. Stent 66 is radially expanded (and axially shortened) over its entire length. Accordingly, inner tube 26 can be withdrawn proximally through expanded stent 66. Proximal transition region 50 further insures against the possibility of enlargement feature 46 being caught during attempted withdrawal, either by stent 66 or a stricture in the body lumen. However, as a precaution against this event, the physician can advance outer tube 18 distally through deployed stent 66 until its distal end once again surrounds the enlargement feature as shown in FIG. 1.

As shown in FIG. 3, stent 66 is in a reduced-radius and axially elongated configuration. Stent 66 is compressed into this configuration due to the external radial force provided by outer tube 18. When outer tube 18 is withdrawn, thus removing the external force, stent 66 assumes a normal or relaxed configuration shown schematically in FIGS. 4 and 19. Typical dimensions for stent 66 that is to be used in the esophagus are 20 mm for the diameter of medial region 70 and about 30 mm for the diameter of the cuffed end regions 72 and 74. The filaments forming the stent are about 0.22 mm or less in diameter.

Preferably a substantial portion of stent 66 is covered with a polymeric film. While a portion of cuffs 72 and 74 are open, medial region 70 is circumscribed, i.e. completely covered, with a continuous polymeric film, preferably silicone. The silicone film is applied by dip coating stent 66 in a bath of silicone rubber and an organic solvent. Preferably 18% silicone rubber to organic solvent, typically xylene, is used. The preferred thickness of the silicone film is in the range of 0.003–0.01 inches (0.076–0.25 mm), and is controlled primarily by the number of dip coating applications. More specifically, from three to five dip coatings result in a thickness within the preferred range.

Figure 21:
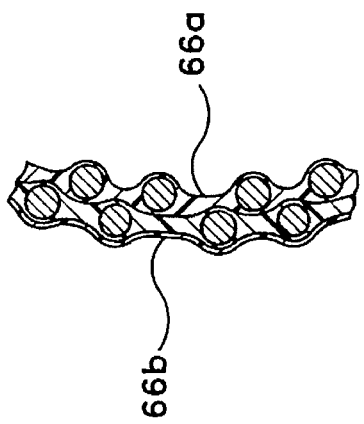
FIG. 21 is an enlarged sectional view of a portion of FIG. 20.
Figure 19:
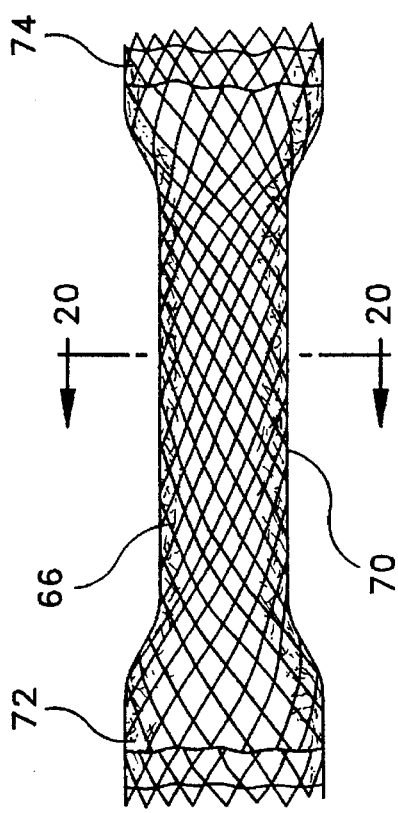
FIG. 19 is a side elevational view of the third embodiment of the stent of this invention in a relaxed configuration.
Figure 20:
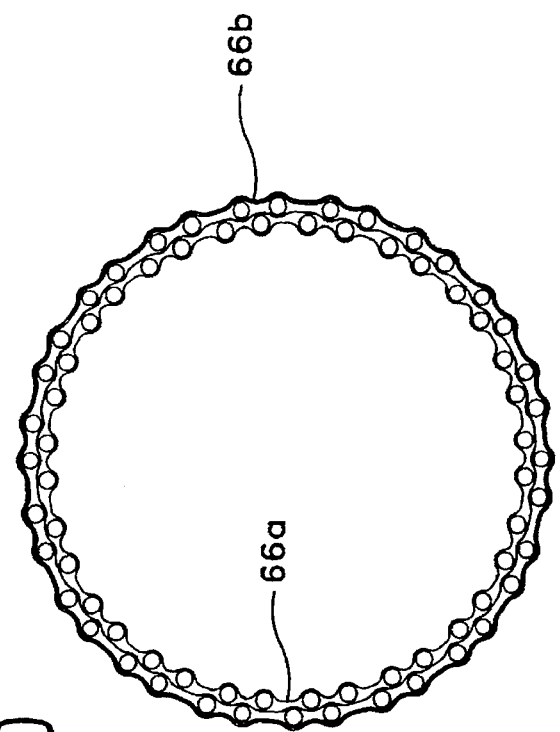
FIG. 20 is a sectional view taken along line 20—20 in FIG. 19.

Stent 66 can be comprised of multiple layers. For example, as shown in FIGS. 19–21, stent 66 is formed from two layers or tubes of wire braided mesh to provide a stent within a stent configuration. Inner stent 66a and outer stent 66b have substantially the same dimensions except that the cuffed regions of outer stent 66b have a shorter axial length than the cuffed regions of inner stent 66a. Providing outer stent 66b with shorter cuffs minimizes the number of bare wires located at the ends of the stent. Preferably the length of the cuffs of outer stent 66b is about one and one-half times the axial distance between the points where the wires of the outer stent 66b cross.

The silicone covering for this embodiment is first applied to outer stent 66b by the process described above. Next inner stent 66a is inserted inside outer stent 66b. It is important that the filaments of the cuffed regions of inner stent 66a line up with the filaments of the cuffed regions of outer stent 66b. This facilitates loading of stent 66 on the delivery device. As shown in FIG. 21, it is not necessary for the filaments in the body of inner stent 66a and outer stent 66b to line up. Finally, the entire structure is dip coated once in the silicone bath.

This arrangement provides a strong barrier region that is effective in preventing tissue ingrowth through the stent and in supporting the flow of fluid or other media therethrough. This results from the silicone being "sandwiched" between the layers of the thread elements forming stent 66. The silicone is reinforced and thus can resist tissue growth through the stent more effectively than a single layer stent.

The silicone film is also elastic and is radially self-expanding like the remainder of stent 66. However, the silicone film reinforces the medial region such that it has a much greater restoring force than the open weave portions of stent 66. In particular, while cuffs 72 and 74, which are not completely coated with silicone, tend to recover virtually instantaneously from a radially compressed configuration, a tumor would inhibit their recovery. Medial region 70 recovers against a tumor, although it has been observed to take 24 hours for recovery. It has been found that the recovery rate of the medial region 70 can be controlled by controlling the thickness of the silicone film.

The gradual recovery rate of medial region 70 against tumors affords several advantages which make stent 66 particularly well suited for treating esophageal strictures. Certain advantages arise from coated medial region 70 itself, and other advantages arise from the combination of medial region 70 with cuffs 72 and 74. Considered alone, medial region 70 provides an effective barrier to tissue ingrowth as well as providing support for the flow of fluids or some other media therethrough, because of the continuous silicone film. The gradual recovery of medial region 70, from the radially compressed state when the stent 66 is deployed, substantially reduces the chance that weakened cancerous tissue will be harmed during stent radial self-expansion. While a recovery rate of about one hour would significantly reduce most of the risk, the observed recovery rate of 24 hours is highly preferred. A further advantage arises from the fact that the residual force along medial region 70 is greater than the residual force along the more rapidly expanding cuffs 72 and 74. As a result, the maximum radial dilating force is provided along that portion of stent 66 aligned with the esophageal stricture.

As mentioned above, cuffs 72 and 74 radially expand rapidly upon their release from a stent confining means such as outer tube 18. Thus, cuffs 72 and 74 rapidly contact and reach equilibrium with healthy tissue of the wall of the body lumen. Thus, cuffs 72 and 74 are particularly effective in resisting either proximal or distal migration of stent 66. The open weave construction of cuffs 72 and 74 is not a problem since medial region 70 is aligned with the defective portion of the body vessel, while cuffs 72 and 74 engage healthy tissue.

Figure 12:
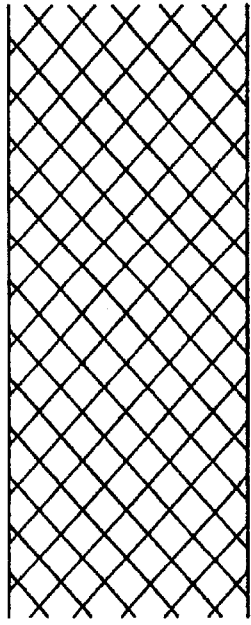
FIGS. 11 and 12 illustrate alternative braid angle configurations for the self-expanding stent of the first embodiment.
Figure 11:
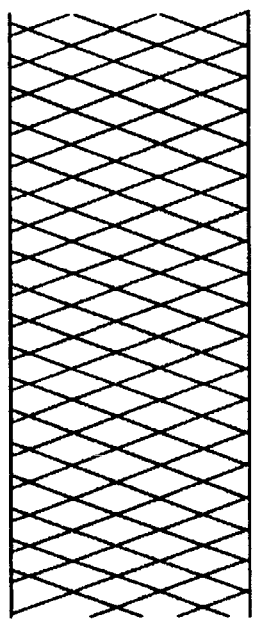

Yet another advantage of the silicone film is that it provides reinforcement along medial region 70, enabling stent 66 to be constructed with a reduced braid angle. The braid angle is measured, based on the filament incline from the axial dimension of stent 66. FIGS. 11 and 12 illustrate a high braid angle and a low braid angle, respectively. In each case, stent 66 is oriented with its axial length in the horizontal direction. Heretofore, 90 degrees has been considered a lower practical limit for the braid angle of a mesh or open weave stent. Employing the silicone film, however, enables a reduction of the braid angle to as low as 70 degrees, as illustrated in FIG. 12. The advantage of a lower braid angle resides in the fact that the braid angle determines the ratio of stent axial shortening to radial increase, as the stent self-expands. With a reduced braid angle, there is less axial shortening for a given radial expansion. Due to the reduced axial "drift", the stent can be more accurately positioned within body lumens during its deployment.

Figure 13:
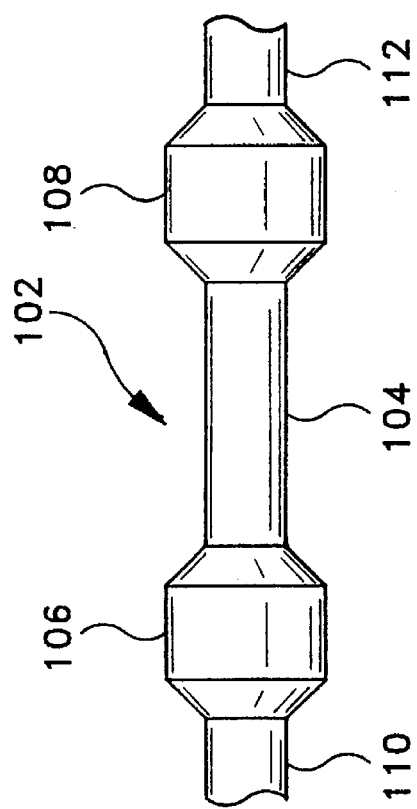
FIG. 13 is a side elevational view showing a mandrel used in forming the stent of FIG. 4.

FIG. 13 illustrates a mandrel 102 particularly well suited for forming stent 66. Mandrel 102 includes a central shank 104, enlargements 106 and 108 on opposite sides of the shank, and end portions 110 and 112. To form stent 66, the individual filaments or strands are wound in helical fashion to form an open weave cylinder. The cylinder is placed upon mandrel 102 and heated to a temperature in the range of from about 800–1,000 degrees F. The filaments, when cooled, retain the shape of the mandrel. Portions of stent 66 formed along the outer ends of the mandrel are trimmed.

Figure 14:
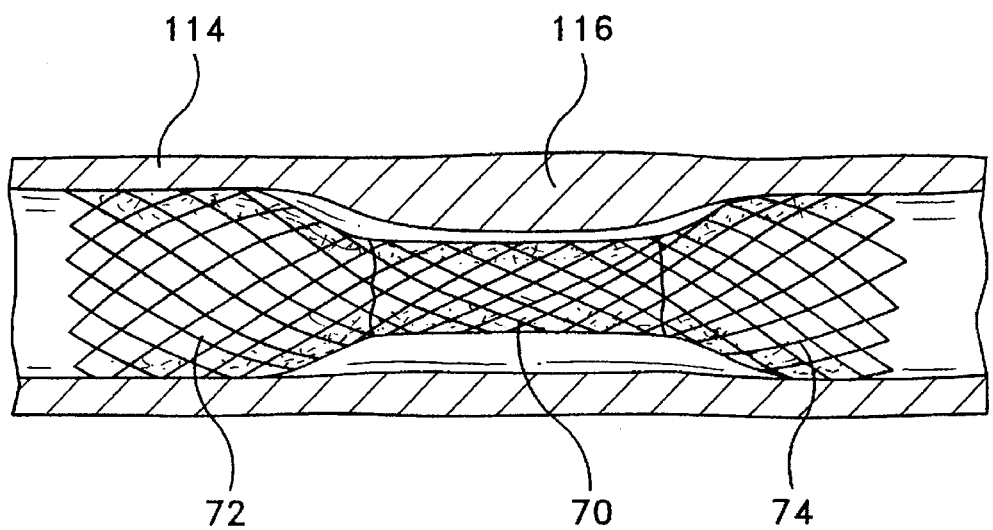
FIG. 14 schematically illustrates a stent in a body lumen a short time after its deployment.
Figure 15:
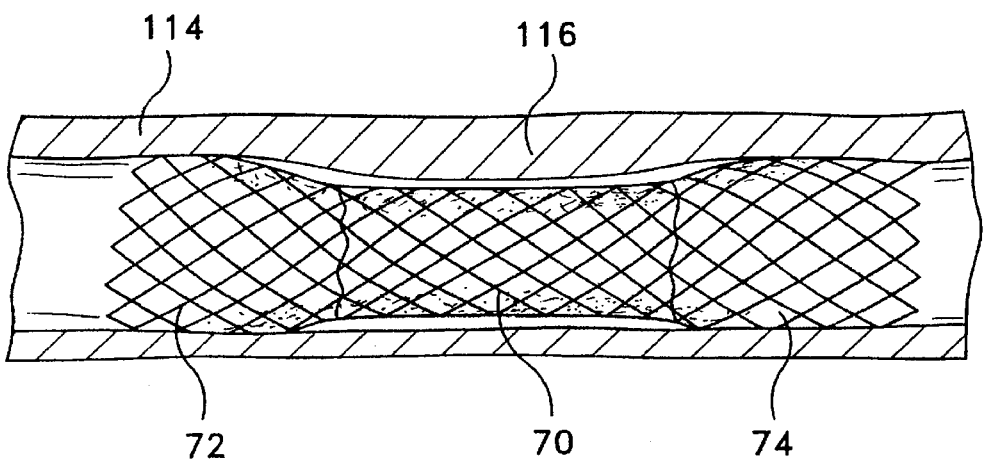
FIG. 15 schematically illustrates a stent one day after its deployment.

FIGS. 14 and 15 schematically illustrate stent 66 after its deployment in the esophagus. A body lumen wall 114 includes a tumor 116. Using a device such as stent delivery device 16, stent 66 is deployed as above explained. Medial region 70 of stent 66 is aligned with the tumor, and cuffs 72 and 74 are aligned with healthy portions of the wall 114 proximally and distally of tumor 116. Cuffs 72 and 74 expand into engagement and equilibrium with wall 114 substantially immediately after deployment. Medial region 70, while it may engage tumor 116, remains radially reduced.

FIG. 15 illustrates stent 66 one day after deployment. Medial region 70 has recovered, and presses against tumor 116 to maintain the patency of the body lumen past the stricture. The diameter of medial region 70 at equilibrium is likely to be greater than two-thirds of the cuff diameter at equilibrium, because of the greater residual force due to the silicone film.

Figure 16:
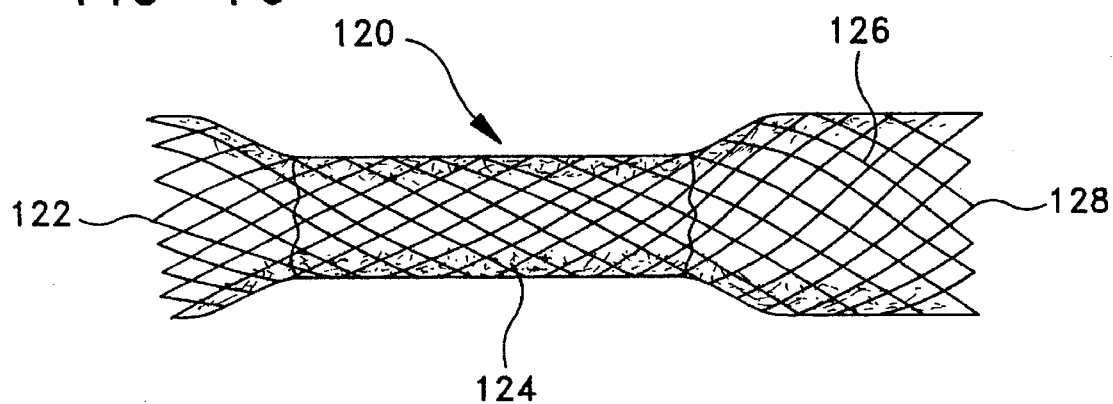
FIG. 16 illustrates a second embodiment of a stent constructed according to the present invention.

FIG. 16 illustrates another alternative stent design having a flared distal end 122. This configuration is used where distal end 122 extends into a body cavity and is used to conform more closely with the body anatomy. Accordingly, stent 120 includes a distal region 124 circumscribed with a continuous silicone film, and a proximal cuff 126 of mesh or open weave construction. Stent 120 can be deployed with a tool substantially identical to deployment device 16.

Thus, it is seen that a radially self-expanding stent with a barrier region circumscribed by a silicone film to reduce tissue ingrowth and to provide a passageway for the flow of media through the stent is provided. The stent is also resistant to migration. In addition, a delivery device is provided for delivering and deploying the stent to the treatment site. This device incorporates a low durometer stent restraining sleeve that fixes the stent axially with respect to an inner tube of the delivery device for enhanced accuracy in stent positioning and enhanced ability to recapture a partially deployed stent.

The invention claimed is:

1. A stent comprising:
   a first layer of material defining a generally hollow, tubular construction;
   a second layer of material comprising a plurality of thread elements helically wound around a longitudinal axis to provide a self-expanding braided mesh construction and defining a generally hollow, tubular construction disposed inside of the first layer of material; and
   a layer of polymeric material disposed between the first layer of material and the second layer of material.

2. The stent of claim 1 wherein the first layer of material comprises a plurality of thread elements helically wound around a longitudinal axis to provide a self-expanding braided mesh construction.

3. The stent of claim 1 wherein at least one of the first layer of material or the second layer of material has a proximal portion, a distal portion and a medial portion located between the proximal portion and the distal portion and wherein at least one of the proximal portion or the distal portion has a diameter larger than the diameter of the medial portion when the stent is in an unconstrained condition.

4. The stent of claim 2 wherein at least one of the first layer of material or the second layer of material has a proximal portion, a distal portion and a medial portion located between the proximal portion and the distal portion and wherein at least one of the proximal portion or the distal portion has a diameter larger than the diameter of the medial portion when the stent is in an unconstrained condition.

5. The stent of claim 1 wherein the second layer of material has a length greater than the length of the first layer of material.

6. The stent of claim 5 wherein the layer of polymeric material extends only along the length of the first layer of material.

7. The stent of claim 5 wherein at least one of the first layer of material or the second layer of material has a proximal portion, a medial portion and a distal portion and wherein at least one of the proximal portion or the distal portion has a diameter larger than the diameter of the medial portion when the stent is an unconstrained condition.

8. The stent of claim 6 wherein at least one of the first layer of material or the second layer of material has a proximal portion, a medial portion and a distal portion and wherein at least one of the proximal portion or the distal portion has a diameter larger than the diameter of the medial portion when the stent is an unconstrained condition.

9. A multiple layer stent comprising:

an outer generally hollow tubular stent formed from at least one thread element helically wound around a longitudinal axis of the multiple layer stent to provide a braided mesh construction;

an inner generally hollow tubular self-expanding stent coaxially disposed within the outer stent and formed from at least one thread element helically wound around a longitudinal axis of the multiple layer stent to provide a braided mesh construction; and a layer of polymeric material covering at least a portion of the multiple layer stent.

10. The multiple layer stent of claim 9 wherein the inner stent has an axial length greater than the axial length of the outer stent.

11. The multiple layer stent of claim 10 wherein the layer of polymeric material extends along at least the length of the outer stent.

12. The multiple layer stent of claim 9 wherein the inner stent and outer stent both have a proximal portion, a medial portion and a distal portion wherein at least one of the proximal portion or the distal portion of both the inner stent and the outer stent have a diameter larger than the diameter of the medial portion when the multiple layer stent is in an unconstrained condition.

13. The multiple layer stent of claim 10 wherein the inner stent and outer stent both have a proximal portion, a medial portion and a distal portion wherein at least one of the proximal portion or the distal portion of both the inner stent and the outer stent have a diameter larger than the diameter of the medial portion when the multiple layer stent is in an unconstrained condition.

14. The multiple layer stent of claim 11 wherein the inner stent and outer stent both have a proximal portion, a medial portion and a distal portion wherein at least one of the proximal portion or the distal portion of both the inner stent and the outer stent have a diameter larger than the diameter of the medial portion when the multiple layer stent is in an unconstrained condition.

15. A stent comprising:

a first layer of material having an axial length and defining a generally hollow, tubular construction;

a second layer of material having an axial length greater than the axial length of the first layer and defining a generally hollow, tubular construction disposed inside of the first layer of material; and a layer of polymeric material disposed between the first layer of material and the second layer of material.

16. The stent of claim 15 wherein at least one of the first layer of material or the second layer of material is a plurality of thread elements helically wound around a longitudinal axis of the first layer of material to provide a braided mesh construction.

17. The stent of claim 15 wherein the layer of polymeric material extends only along the length of the first layer of material.

18. The stent of claim 15 wherein at least one of the first layer of material or the second layer of material has a proximal portion, a medial portion and a distal portion and wherein at least one of the proximal portion or the distal portion has a diameter larger than the diameter of the medial portion when the stent is an unconstrained condition.

19. The stent of claim 17 wherein at least one of the first layer of material or the second layer of material has a proximal portion, a medial portion and a distal portion and wherein at least one of the proximal portion or the distal portion has a diameter larger than the diameter of the medial portion when the stent is an unconstrained condition.

20. A multiple layer stent comprising:

an outer generally hollow tubular stent having an axial length formed from at least one thread element helically wound around a longitudinal axis of the multiple layer stent to provide a braided mesh construction;

an inner generally hollow tubular stent greater than the axial length of the outer stent and coaxially disposed within the outer stent and formed from at least one thread element helically wound around a longitudinal axis of the multiple layer stent to provide a braided mesh construction; and a layer of polymeric material covering at least a portion of the multiple layer stent.

21. The multiple layer stent of claim 20 wherein the layer of polymeric material extends along at least the length of the outer stent.

22. The multiple layer stent of claim 20 wherein the inner stent and outer stent both have a proximal portion, a medial portion and a distal portion wherein at least one of the proximal portion or the distal portion of both the inner stent and the outer stent have a diameter larger than the diameter of the medial portion when the multiple layer stent is in an unconstrained condition.

* * * * *